(12) United States Patent
Lanze et al.

(10) Patent No.: US 6,689,464 B1
(45) Date of Patent: Feb. 10, 2004

(54) METHOD AND DEVICE FOR PRODUCING BISPHENOL A PRILLS AND BISPHENOL A PRILLS PRODUCED ACCORDING TO THIS METHOD

(75) Inventors: Rolf Lanze, Krefeld (DE); Alfred Eitel, St. Johann (AT); Rainer Neumann, Krefeld (DE); Steffen Kühling, Meerbusch (DE); Frieder Heydenreich, Düsseldorf (DE); Tony van Osselaer, Krefeld (DE); Rainer Bellinghausen, Odenthal (DE); Heiko Herold, Neuss (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/869,773

(22) PCT Filed: Jan. 5, 2000

(86) PCT No.: PCT/EP00/00041

§ 371 (c)(1),
(2), (4) Date: Aug. 31, 2001

(87) PCT Pub. No.: WO00/40533

PCT Pub. Date: Jul. 13, 2000

(30) Foreign Application Priority Data

Jan. 7, 1999 (DE) .......................... 199 00 221

(51) Int. Cl.[7] .............. B32B 5/16; B29B 9/00; C07C 37/64
(52) U.S. Cl. ............ 428/402; 55/309.1; 55/410.1; 55/476; 264/13; 425/6; 425/72.1; 568/703; 568/723; 568/724

(58) Field of Search .............. 428/402; 264/13; 55/309.1, 410.1, 476; 568/703, 723, 724; 425/6, 72.1

(56) References Cited

U.S. PATENT DOCUMENTS

| 3,975,472 | A | * | 8/1976 | Packbier et al. | 264/14 |
| 4,813,982 | A | * | 3/1989 | Huey et al. | 95/288 |
| 4,935,173 | A | * | 6/1990 | Huey et al. | 264/14 |
| 4,954,661 | A | * | 9/1990 | Iimuro et al. | 568/727 |
| 5,354,520 | A | * | 10/1994 | Oliver et al. | 264/3.4 |
| 5,362,223 | A | * | 11/1994 | Gneuss | 425/185 |
| 5,371,302 | A | * | 12/1994 | Yanai et al. | 568/703 |
| 6,586,637 | B2 | * | 7/2003 | Iwahara | 568/728 |

FOREIGN PATENT DOCUMENTS

EP 0 278 246 8/1988

OTHER PUBLICATIONS

**Patents Abstract of Japan, vol. 018, No. 385 (C–1227), Jul. 20, 1994, & JP 06 107581 A (Nippon Steel Chem. Co. Ltd; Others: 01), Apr. 19, 1994.

* cited by examiner

Primary Examiner—H. Thi Le
(74) Attorney, Agent, or Firm—Joseph C. Gil; Aron Preis

(57) ABSTRACT

A method for producing bisphenol A in prill form is disclosed. Molten bisphenol is top-fed into a prilling tower via a plate containing a plurality of nozzles. A gas coolant guided through a circuit is led into said tower in a counter flow direction. The prills are cooled to about room temperature, collected at the bottom of the tower and removed. Also disclosed is the device for carrying out the inventive method and the prills thus produced.

26 Claims, 3 Drawing Sheets

Figure 1:
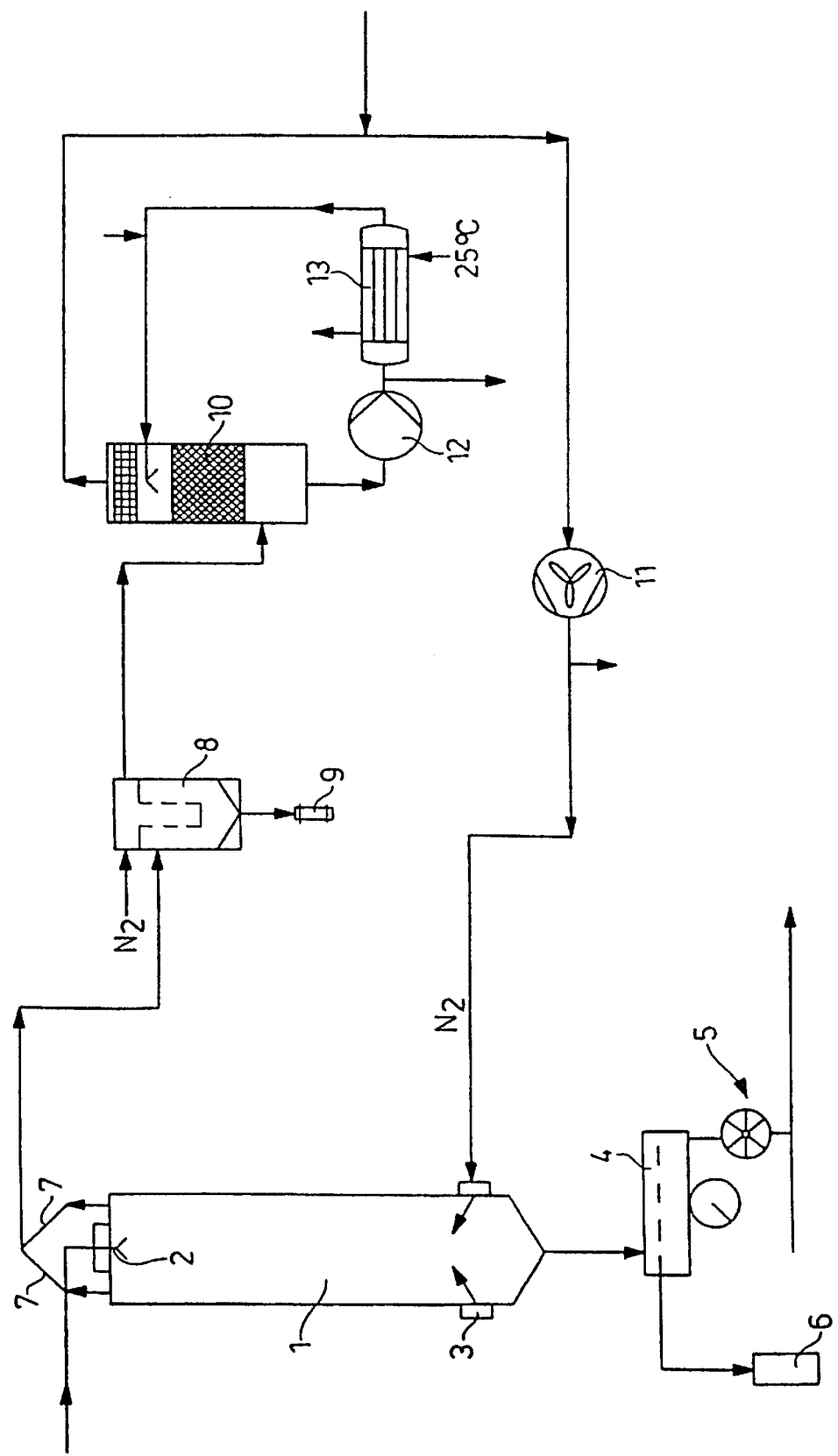

METHOD AND DEVICE FOR PRODUCING BISPHENOL A PRILLS AND BISPHENOL A PRILLS PRODUCED ACCORDING TO THIS METHOD

The invention relates to a process for the preparation of bisphenol-A prills, wherein molten bisphenol-A is charged into a prilling tower at the top of the prilling tower via a nozzle plate with a plurality of nozzles, into which prilling tower a cooling gas which is conducted in a circuit is introduced in counter-flow and wherein the bisphenol-A prill which has cooled to approximately room temperature is collected at the base of the prilling tower and is withdrawn, and moreover to a device for implementing such a process, and also to a bisphenol-A prill that is prepared in accordance with this process.

Bisphenols are chemical compounds with two phenol groups, obtained by causing phenol to react with ketones, whereby bisphenol-A (2,2-bis(4-hydroxyphenyl)propane) is formed as a result of the reaction of phenol and acetone. Bisphenol-A is processed further into epoxy resins, polycarbonates and polysulfones. With a view to alleviating pouring, transport and storage, granular material, flakes or prills are prepared from a bisphenol-A melt by cooling, whereby prills present advantages in comparison with granular material or flakes, by reason of their lower proportion of dust and better flow properties.

A process for the preparation of bisphenol-A prills is known from JP-6-107 581, wherein molten bisphenol-A is charged in the top region of a prilling tower and cooling gas, which abstracts the heat of fusion from the falling droplets of melt, is introduced in counter-flow at the base of the prilling tower. The solidified prills are withdrawn at the base of the prilling tower.

The aim of the known process was to increase the hardness of the bisphenol-A prills which are prepared, in order to reduce the proportion of dust. However, depending on the type of further processing, in addition to the very low dust content still further demands are made of prills.

The object underlying the present invention is therefore to create a process and a device for the preparation of bisphenol-A prills and to create prills which are prepared accordingly in which the purity of the product is of prime importance. In order to obtain bisphenol-A prills that are as pure as possible, on the one hand their monophenol contents and residual dust content are to be reduced, and on the other hand a particularly clear and also colour-stable product is to be created.

With regard to the process, this object is achieved by the charge of the bisphenol-A melt and the introduction of the cooling gas being effected uniformly in distributed manner over the cross-section of the prilling tower.

As far as the device is concerned, the solution is obtained by an annular line which is guided horizontally into the prilling tower and which tapers in cross-section being provided for uniform feed of cooling gas, by a baffle plate for dividing the current of cooling gas into two partial currents being provided in the radially flange-mounted cooling-gas-channel input, and by a plurality of honeycombed rectifier elements being provided, arranged uniformly over the periphery of the prilling tower. In this way it is possible, in accordance with the invention, to distribute the cooling gas in twist-free manner and directed towards the cross-section of the prilling tower.

With the process according to the invention and the device according to the invention it is possible for prills to be prepared, the dust proportion of which is below 2% by mass, which possess an inherent colour of less than 10 Haze and which exhibit a BET surface of >0.15 $m^2/g$. The particle size dp amounts to between 0.5 and 3 mm, preferably between 0.8 and 2 mm.

The process is described more fully in the following. Essential for the process for low-phenol and low-dust preparation of bisphenol-A prills is a temperature setting of the bisphenol-A melt that is as exact as possible for nozzle atomisation within a wide working range. This temperature control is preferably made possible by means of a shell-and-tube exchanger. In the process the bisphenol-A melt is preferably obtained at 185° C. to 250° C. In the aforementioned shell-and-tube exchanger the bisphenol-A melt is cooled down to a temperature close to the crystallisation temperature of 156° C. The temperature of the bisphenol-A melt which is charged into the prilling tower preferably amounts to 165° C.

For the purpose of temperature control, according to a further teaching of the invention a 3-chamber shell-and-tube exchanger is expediently employed, whereby, with a view to cooling, the melt is passed through the tubes of the shell-and-tube exchanger. In the outer chamber around the tubes pressurised water is fed in and evaporated, in order to abstract heat from the bisphenol-A melt. The temperature of the melt is set both by the evaporation pressure of the water and via the number of the tubes which are surrounded by pressurised water. Since the radiator side of the heat exchanger is operated at below the crystallisation temperature of bisphenol-A, the heat exchanger is equipped with an additional heating jacket. During the critical phases—that is to say, in the course of start-up or in low-load operation, for example—freezing-up on the product side is reliably prevented by feeding a heat carrier into said heating jacket.

In a further refinement of the invention a purification of the melt is undertaken in a melt filter immediately prior to the charge of the bisphenol-A melt into the prilling tower. Metallic-cloth sieves with a mesh size of <80 $\mu m$ are preferably employed for this filtration.

In a further refinement of the invention the nozzle plate for the charge of melt is operated under a slight excess pressure in the range from 0.05 to 1 bar, preferably between 0.15 and 0.3 bar. The differential pressure is substantially determined by the geometry of the bores, the number of bores per nozzle plate, the temperature of the melt and the feed quantity (volumetric flow rate). With a view to uniform distribution of the bisphenol-A melt, the nozzle plate is preferably spherically domed and arranged centrally on the top of the prilling tower. Moreover, in a further refinement of the invention several discharge pipes are arranged in the upper part of the prilling tower, uniformly distributed over the cross-section of the prilling tower, via which the cooling gas is withdrawn. These discharge pipes are expediently constructed with attendant heating. In this way it is possible for deposits of product to be reliably prevented.

By reason of the fact that the cooling gas is conducted in a circuit, a purification of the cooling gas has to be undertaken, which is preferably realised in the form of a bag filter.

A further teaching of the invention provides for the cooling gas which is conducted in a circuit to be continuously cooled and freed of monophenols, cooling preferably being undertaken in a washing tower with secondary cooling circuit. By this means the physical size of the cooling circuit is clearly reduced, and continuous operation is also only possible by virtue of this configuration, since, in the case of shell-and-tube exchangers which are employed for the purpose of cooling, said exchangers can always only be employed as reversible exchangers, in order to enable the phenol to be separated from the recycled nitrogen by freezing.

Cooling of the cooling gas which is conducted in a circuit is preferably undertaken with demineralised water without dissolved oxygen, in order reliably to avoid formation of foam.

Figure 2:
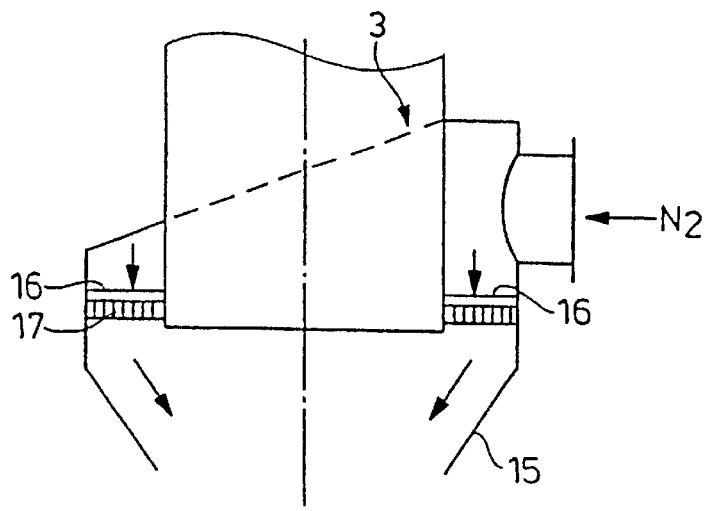
Figure 3:
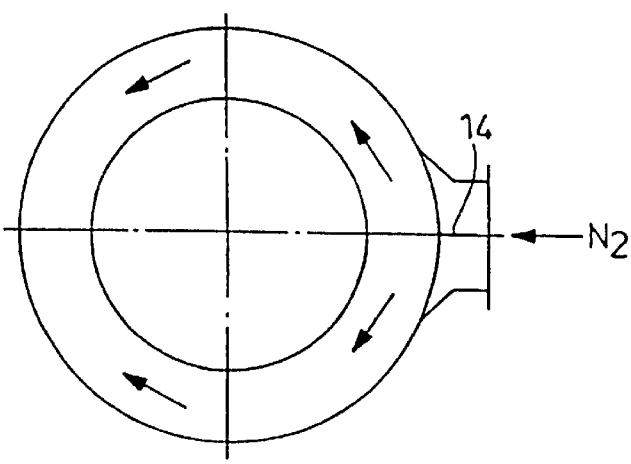
Figure 4:
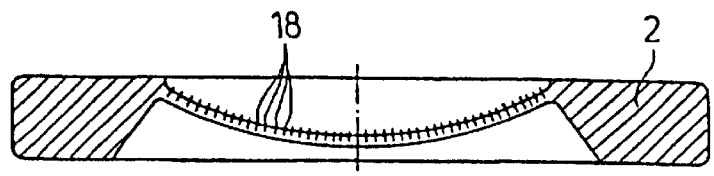
Figure 5:
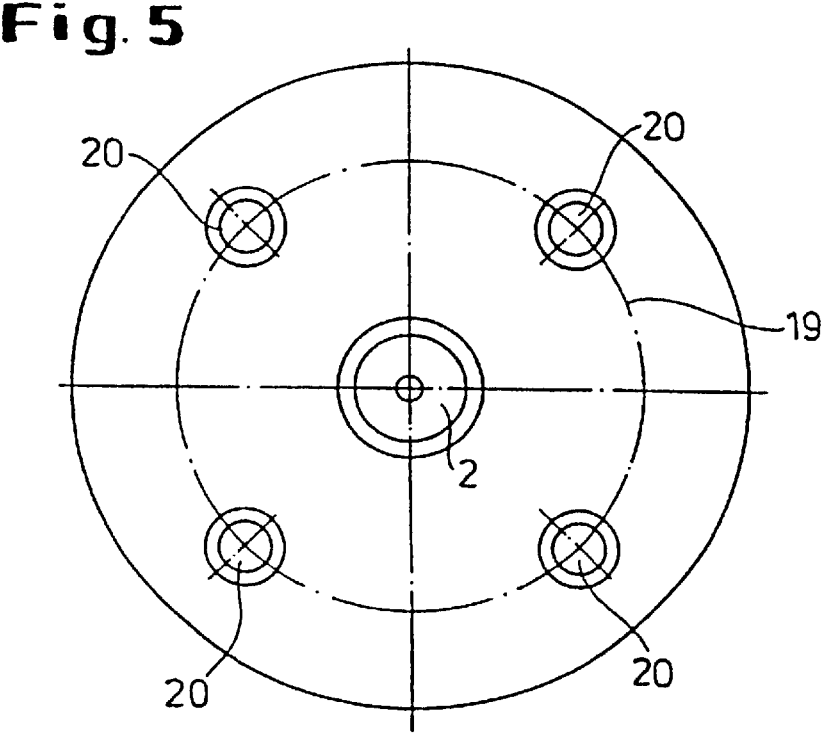
Figure 6:
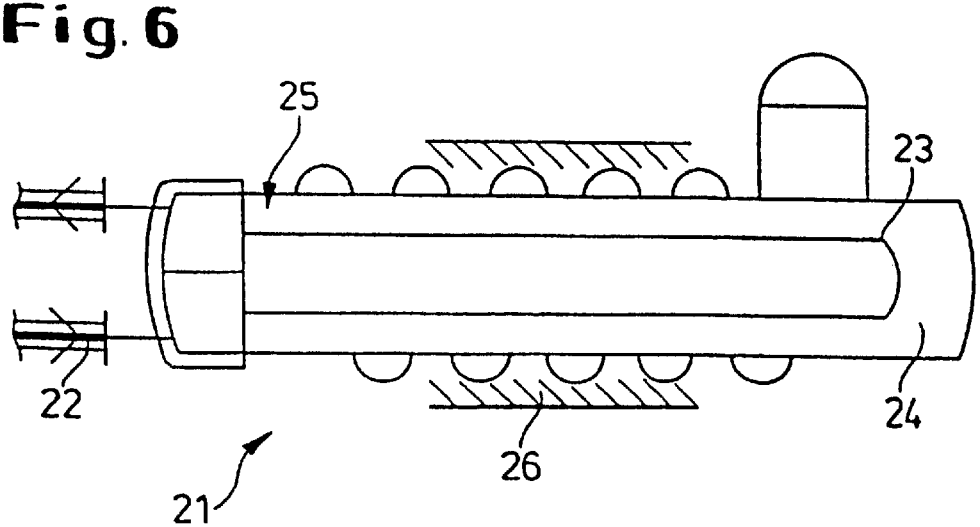

The device according to the invention is elucidated more fully in the following on the basis of a drawing representing a preferred embodiment. Shown in the drawing are:

FIG. 1 a schematic representation of the process according to the invention for the preparation of bisphenol-A prills, FIG. 2 the base region of the prilling tower in cross-section, FIG. 3 the base region of the prilling tower in horizontal section in schematic representation, FIG. 4 a cross-section through the nozzle plate which is used for the nozzle-injection of melt, FIG. 5 the schematic arrangement of cooling-gas removal pipes and melt input at the top of the prilling tower and FIG. 6 a melt cooler for temperature-control of the bisphenol-A prill to be charged, schematically in cross-section.

In FIG. 1 an overall view of the device according to the invention for the preparation of bisphenol-A prills is represented with recycling of cooling gas. The BPA melt which is temperature-controlled in a melt cooler, which is not represented, is charged into a prilling tower 1 by atomisation via a nozzle plate 2 which is only represented schematically. In order to utilise the entire cross-section of the prilling tower for the intensive exchange of heat and material between bisphenol and cooling gas, the nozzle plate 2 is arranged centrally on the top of the prilling tower 1. Cooling gas, preferably nitrogen ($N_2$), is introduced in counter-flow at the base of the prilling tower 1 via a cooling-gas distributor 3. By this means the charged droplets of BPA melt are cooled and solidified into bisphenol-A prills. The prills are collected in a cone at the base of the prilling tower 1, freed of coarse particles via a sieve 4, and transported into storage silos via, for example, a pneumatic conveyor system 5. The oversize material is collected in a container 6. The heated cooling gas is removed at the top of the prilling tower via several discharge pipes 7 and is freed of entrained ultrafine dust in a solids filter 8. The ultrafine dust, like the oversize material, is collected in a dust container 9 with a view to further use.

Subsequently the cooling gas is cooled in a washing tower 10 and freed, by intensive contact with the washing liquid, of the readily volatile monophenols that have been stripped off, before it is supplied again to the prilling tower 1 as cooling gas. The circuit operation is maintained with the aid of a fan 11.

As is evident from FIG. 1, the cooling liquid pertaining to the washing tower 10 is preferably operated likewise in a circuit. The heated washing liquid is supplied by means of a pump 12 to a heat exchanger 13, is cooled there and subsequently passed to the top of the washing tower 10. In order to avoid concentration of washed-out phenols, a partial quantity is constantly discharged from the cooling circuit and replaced by fresh washing liquid, as indicated by the two arrows in the washing-liquid circuit.

For optimal cooling and stripping-off of the bisphenol-A melt, a uniform, intensive contact between cooling gas and drops of melt is required. Particularly important therefore is the rapid attainment of a fully formed, upward-directed, twist-free flow of the cooling gas in the prilling tower 1. This is achieved by virtue of the cooling-gas distributor 3 according to the invention, which is shown in FIGS. 2 and 3.

The current of cooling gas enters the cooling-gas distributor 3 radially and is split up into two equally large components by a baffle plate 14. Both currents are conveyed tangentially around the prilling tower 1 in a distributor housing. In the peripheral direction of the prilling tower 1 a partial quantity of the cooling gas is constantly conducted away in the vertical direction towards the cone 15 at the base of the prilling tower 1. Perforated plates 16 provide for equal distribution of the quantity of cooling gas flowing away over the periphery of the prilling tower 1. Equal distribution is assisted furthermore by a constant cross-sectional tapering, clearly visible in FIG. 2, of the distributor channel around the prilling tower 1.

According to the invention, rectifier elements 17, the preferred length/diameter ratio of which is greater than 5, are arranged beneath the perforated plates 16. Through the use of these rectifier elements 17, which are expediently assembled from honeycombed into rectifier packings, a downward-directed, uniform flow to the cone 15 is brought about. In the region of the cone the quantity of cooling gas is turned around by 180° and, after a short inlet section, flows upwards through the prilling tower 1, distributed uniformly over the entire cross-section.

A nozzle plate 2, which is preferably spherically formed, is represented in FIG. 4. A plurality of bores 18 are uniformly distributed on the surface of the nozzle plate 2. As has already been explained, the nozzle plate 2 is operated at a slight differential pressure, in order to be able to guarantee the residual-phenol and dust specifications that are demanded. Since the differential pressure is substantially determined by the geometry of the bores 18, the number of bores 18 per nozzle plate 2, the temperature of the BPA melt and the feed quantity, interchangeable nozzle plates 2 are expediently present for differing load adaptations, in order to attain an optimal distribution, for each load range, of the droplets of melt over the cross-section of the prilling tower 1.

The upper region of the prilling tower 1 also has to be as free as possible from transverse flows, in order to guarantee uniform contact of cooling gas and drops of melt over the entire height of the prilling tower. This assumes that the directed upward flow, in particular also in the top region—that is to say, in the location of the nozzle-injection of melt, is barely perturbed. Drainage of gas at the top of the prilling tower is therefore effected by means of several, preferably three to four, discharge pipes 20 which are arranged symmetrically on a hole circle 19, as shown schematically in FIG. 5. The discharge pipes 20 are brought together, in a manner favourable to flow, in a collecting pipe, which is not represented, of, equivalent cross-section. In this way the previously described arrangement of the discharge pipes 20 enables centric nozzle-injection of the bisphenol-A melt by means of the nozzle plate 2. The discharge pipes 20 are expediently constructed with attendant heating.

Finally, a melt cooler 21 which is employed for temperature control of the BPA melt is represented schematically in FIG. 6. The melt cooler 21 is constructed as a 3-chamber shell-and-tube exchanger. The BPA melt which is obtained in the process preferably at temperatures between 185° C. and 250° C. is passed via an input 22 through pipes 23 pertaining to the melt cooler. In the outer chamber 24 around the pipes 23 pressurised water 25 is fed in and evaporated. Heat is abstracted from the BPA melt by this means. Since the radiator side of the heat exchanger is operated at below the crystallisation temperature of BPA (156° C.), the melt cooler 21 is equipped with an additional heating jacket 26. As a result of feeding a heat-carrier 27 (vapour, for example) into this heating jacket 26, freezing-up on the product side during the start-up phase or at low-load operation of the prilling process is reliably ruled out.

EXAMPLE

Bisphenol-A melt with a GC purity of 99.69% by mass is continuously charged at the top of the prilling tower and turned into bisphenol-A prills by the process according to the invention. The bisphenol-A prills obtained in this way are distinguished by a lower total phenol content (phenol, isopropyl-phenol and t-butyl-phenol contents), whereby, in comparison with the charged bisphenol-A melt, a reduction in the phenol content by 40 ppm to 10 ppm, in the isopropenyl-phenol content by 20 ppm to 10 ppm and in the t-butyl-phenol content by 60 ppm to 20 ppm was able to be brought about as a result of the prilling operation. The prills exhibit a BET surface of 0.17 $m^2/g$ and an inherent colour of 5 Haze (DIN 59 409).

The high quality of the bisphenol-A prills according to the invention also results in excellent stability in storage. This good stability in storage shows itself in that bisphenol-A prills with an inherent colour of 5 Hz that have been stored for over a month in daylight and at room temperature still possess an inherent colour of 5 Hz. On the other hand, for a comparison, a bisphenol-A melt with higher proportions of phenol (phenol content 50 ppm, isopropenyl-phenol content 30 ppm and t-butyl-phenol content 80 ppm) shows an Hz colour index of 15 Hz after the same treatment.

The advantages of low-dust, stable-in-storage, brightly coloured bisphenol-A prills with a large BET surface show themselves in particular in the course of further processing of the bisphenol A into polycarbonate. With a view to preparing 1.022 t of a 15-% aqueous solution of sodium bisphenol-A, 154.5 kg of bisphenol-A prills are dissolved within 14 min in 867.5 kg 6.5-% NaOH with stirring and under inert conditions (the entire process is rendered inert with nitrogen). The Hz colour index of this solution subsequently amounts to 0.9 Hz. Such an NaBPA solution is then employed immediately for the preparation of polycarbonate in accordance with the interphase process, which is known as such. The YI (yellowness index) of the polycarbonate which is formed with a relative solution viscosity of 1,200 amounts to 1.48. The good quality of such a polycarbonate results in a particularly high-grade quality of the mouldings that are produced therefrom.

What is claimed is:

1. Process for the preparation of bisphenol-A prills, wherein molten bisphenol-A is charged into a prilling tower at the top of the prilling tower via a nozzle plate with a plurality of nozzles, into which prilling tower a cooling gas which is conducted in a circuit is introduced in counter-flow and wherein the bisphenol-A prill which has cooled to approximately room temperature is collected at the base of the prilling tower and is withdrawn, characterised in that the charge of the bisphenol-A melt and the introduction of the cooling gas are uniformly distributed over the cross-section of the prilling tower.

2. Process according to claim 1, characterised in that the temperature of the bisphenol-A melt at the input is 160° C. to 170° C.

3. Process according to claim 2, characterised in that the temperature of the bisphenol-A melt at the input is 165° C.

4. Process according to claim 1 characterised in that a purification of melt is undertaken in a melt filter immediately prior to the charge of the bisphenol-A melt into the prilling tower.

5. Process according to claim 1 characterised in that the nozzle plate is operated under a slight excess pressure in the range from 0.05 to 1 bar.

6. Process according to claim 1 characterised in that the cooling gas in the upper part of the prilling tower is withdrawn through several discharge pipes which are uniformly distributed over the cross-section of the prilling tower.

7. Process according to claim 6, characterised in that the discharge pipes are subject to attendant heating.

8. Process according to claim 1 characterised in that the cooling gas which is conducted in a circuit is mechanically filtered.

9. Process according to claim 1 characterised in that the cooling gas which is conducted in a circuit is continuously cooled.

10. Process according to claim 9, characterised in that cooling of the cooling gas is undertaken in a washing tower with secondary cooling circuit.

11. Process according to claim 10, characterised in that the cooling of the cooling gas which is conducted in a circuit is undertaken with demineralised water without dissolved oxygen.

12. The process of claim 1 wherein molten bisphenol A is purified in a melt filter immediately prior to charging into said prilling tower.

13. Device for the preparation of bisphenol-A prills by implementing the process according to claim 1 comprising a prilling tower, a bisphenol-A melt feed, a cooling-gas circuit with fan and cooler, a bisphenol-A prill drain, characterised in that an annular line which is guided horizontally into the prilling tower (1) and which tapers in cross-section is provided for uniform feed of cooling gas, in that a baffle plate (14) for dividing the current of cooling gas into two partial currents is provided in the radially flange-mounted cooling-gas-channel input and in that a plurality of honeycombed rectifier elements (17) are provided, arranged uniformly over the periphery of the prilling tower (1).

14. Device according to claim 13, characterised in that use is made of a melt filter upstream of the input of the bisphenol-A-melt.

15. Device according to claim 14, characterised in that a metallic-cloth sieve with a mesh size less than 80 µm is provided by way of melt filter.

16. Device according to claim 13 characterised in that a melt cooler (21) is provided for the purpose of temperature control of the bisphenol-A melt.

17. Device according to claim 16, characterised in that a shell-and tube cooler is provided by way of melt cooler (21).

18. Device according to claim 17, characterised in that a 3-chamber shell-and-tube cooler is provided by way of shell-and-tube cooler.

19. Device according to claim 13 characterised in that the nozzle plate (2) is spherically domed.

20. Device according to claim 13 characterised in that a plurality of discharge pipes (20) arranged symmetrically on a hole circle (19) are provided in the top region of the prilling tower (1) for the dranage of cooling gas.

21. Device according to claim 20, characterised in that the several discharge pipes (20) are combined symmetrically outside the prilling tower (1) into a single discharge pipe.

22. Bisphenol-A prills prepared in accordance with the process according to claim 1 characterised in that the proportion of dust in the prills at the outlet of the prilling tower is below 2% by mass.

23. Bisphenol-A prills prepared in accordance with the process according to claim 1 characterised in that the BET surface of the prills is greater than 0.15 $m^2/g$.

24. Bisphenol-A prills prepared in accordance with the process according to claim 1 characterised in that the Haze colour index of the prills is less than 10 Hz.

25. Bisphenol-A prills prepared in accordance with the process according to claim 1 characterised by a particle size of 0.5 to 3 mm.

26. Bisphenol-A prills prepared in accordance with the process according to claim 1 characterised in that the particle size is 0.8 to 2 mm.

* * * * *